(12) United States Patent
Chung

(10) Patent No.: US 10,597,740 B2
(45) Date of Patent: Mar. 24, 2020

(54) BIFIDOBACTERIUM LONGUM CBT BG7 STRAIN FOR PROMOTION OF GROWTH AND NUTRACEUTICAL COMPOSITION FOR PROMOTION OF GROWTH CONTAINING THE SAME

(71) Applicant: Cell Biotech Co., Ltd., Gimpo-si (KR)

(72) Inventor: Myung Jun Chung, Seoul (KR)

(73) Assignee: CELL BIOTECH CO., LTD., Gimpo-si (KR)

( * ) Notice: Subject to any disclaimer, the term of this patent is extended or adjusted under 35 U.S.C. 154(b) by 0 days.

(21) Appl. No.: 16/374,885

(22) Filed: Apr. 4, 2019

(65) Prior Publication Data

US 2019/0256934 A1 Aug. 22, 2019

Related U.S. Application Data

(62) Division of application No. 15/310,299, filed as application No. PCT/KR2015/007227 on Jul. 13, 2015.

(30) Foreign Application Priority Data

May 21, 2015 (KR) .................. 10-2015-0071124

(51) Int. Cl.
| | | |
|---|---|---|
| *A61K 39/02* | (2006.01) | |
| *C12R 1/01* | (2006.01) | |
| *C12N 1/20* | (2006.01) | |
| *A23L 33/135* | (2016.01) | |
| *A61K 35/745* | (2015.01) | |
| *A23L 2/52* | (2006.01) | |

(52) U.S. Cl.
CPC .............. *C12R 1/01* (2013.01); *A23L 33/135* (2016.08); *A61K 35/745* (2013.01); *C12N 1/20* (2013.01); *A23L 2/52* (2013.01); *A23V 2002/00* (2013.01); *A23Y 2300/55* (2013.01)

(58) Field of Classification Search
None
See application file for complete search history.

(56) References Cited

U.S. PATENT DOCUMENTS 7,351,739 B2 4/2008 Ho et al.

FOREIGN PATENT DOCUMENTS

| KR | 10-0472865 | 3/2005 |
|---|---|---|
| KR | 10-0530211 | 11/2005 |
| KR | 10-0561286 | 3/2006 |
| KR | 10-0865363 | 10/2008 |
| KR | 10-0887377 | 3/2009 |

OTHER PUBLICATIONS

Collins et al (Journal of Dairy Science vol. 67, No. 7, 1984, pp. 1376-1380).*
Jimenez et al (J Bacteriol. Jul. 2012; 194(14): 3762-3763).*
International Search Report, issued in the corresponding International Application No. PCT/KR2015/007227, dated Aug. 26, 2015, 3 pages.
Kang et al., "Dual Coating Improves the Survival of Probiotic Bifidobacterium Strains during Exposure to Simulated Gastro-Intestinal Conditions", Korean Journal of Microbiology, vol. 49, No. 3, 2013, pp. 275-281.
Kim, "Understanding and utilization of microbial agents for improving livestock environment", Rural Development Administration, Korea National Institute Animal Science, Dec. 2, 2009, 22 pages.
Saljoughian, "Probiotics: A Closer Look", US Pharm., vol. 33, No. 6, 2003, pp. 40-44.
Kitaoka, "Bifidobacterial Enzymes involved in the Metabolism of Human Milk Oligosaccharides", American Society for Nutrition, vol. 3, 2012, pp. 422S-429S.

* cited by examiner

*Primary Examiner* — Jennifer E Graser
(74) *Attorney, Agent, or Firm* — Hamre, Schumann, Mueller & Larson, P.C.

(57) ABSTRACT

The present invention a *Bifidobacterium longum* CBT BG7 Bifidobacterium, which has an excellent growth promoting effect and was internationally deposited with the Korean Collection for Type Culture (KCTC) of the Korea Research Institute of Bioscience and Biotechnology under accession number KCTC 12200BP. The strain of the present invention has a beneficial effect of promoting growth by promoting the digestion of human milk oligosaccharides to enhance immunity together with physical strength.

17 Claims, 5 Drawing Sheets

Specification includes a Sequence Listing.

1: *B. longum*$^T$ (ATCC 15707)
2: *B. longum* BG7 (KCTC 12200BP)

A: β-Galactosidase
B: α-Mannosidase
C: β-Mannosidase
D: Glucosylceramidase
E: Endo-β-N-Acetylglucosaminidase
F: Endo-α-N-Acetylgalactosaminidase
G: Sialidase
H: α-Fucosidase
I: α-N-Acetylglucosaminidase
J: β-N-Acetylglucosaminidase
K: β-N-Acetylhexosaminidase ● Bacteriocin  ● Lantipeptide
● NRPS domain containing-protein

BIFIDOBACTERIUM LONGUM CBT BG7 STRAIN FOR PROMOTION OF GROWTH AND NUTRACEUTICAL COMPOSITION FOR PROMOTION OF GROWTH CONTAINING THE SAME

CROSS-REFERENCE TO RELATED APPLICATIONS

This application is a Division of application Ser. No. 15/310,299, filed Nov. 10, 2016, which is a National Stage application of PCT/KR2015/007227, filed Jul. 13, 2015, which is based upon and claims the benefit of priority from Korean Patent Application No. 10-2015-0071124, filed on May 21, 2015, the contents of which are incorporated herein by reference.

TECHNICAL FIELD

The present invention relates generally to a *Bifidobacterium longum* CBT BG7 strain for promotion of growth and a nutraceutical composition for promotion of growth containing the same, and more particularly to a *Bifidobacterium longum* CBT BG7 strain capable of promoting the growth of neonates, infants, young children, and growing children by promoting the digestion of human milk and synthesizing vitamins, and to a nutraceutical composition for promotion of growth, which contains the *Bifidobacterium longum* CBT BG7 strain.

BACKGROUND ART

Human growth occurs in a period up to adolescence, in which most growth plates are still open. Growth can be medically defined as a change in size accompanying maturation, and particularly, the term "growth of children" is intended to encompass not only an increase in height, but also increases in the size and function of each organ of the body.

It is generally recognized that human growth is most influenced by genetic factors. However, in fact, genetic factors have only about 23% of an influence on human growth, and the remaining 77% is determined by postnatal factors. In recent years, due to continued economic growth, westernized eating habits, improved nutritive conditions, etc., the growth and development of children and teenagers has greatly increased. In addition, with the emphasis of a social atmosphere where external appearances and heights are considered important, growth has been of increasing interest.

Methods for promoting growth, known to date, include methods of administering growth hormone agents. However, the use of growth hormones is very costly and may cause adverse effects, including various symptoms such as pruritus of injection sites, seizures, lipoatrophy, hypertension, glucose intolerance, pancreatitis, systemic allergic responses, growth hormone antibody-positive responses, cancer development, and gynaecomastia in males. Accordingly, there is an urgent need for the development of safe and effective food materials that can essentially assist in growth.

Korean Patent No. 0887377 (entitled "Health supplement food for babies and teenagers"), Korean Patent No. 10530211 (entitled "Functional health food composition for improving learning ability and preparation method thereof"), Korean Patent No. 0561286 (entitled "Health functional composition for promotion of growth and development containing dried yeast, natural extract powder and mixed powder of nutritive components"), etc., suggest foods for promotion of growth. However, these foods have growth promotion effects that fall short of expectations.

DISCLOSURE

Technical Problem

The present inventors have made extensive efforts to discover probiotics having excellent growth promoting effects, and, as a result, have experimentally found the applicability of a *Bifidobacterium longum* CBT BG7 strain as a growth-promoting product, thereby completing the present invention. An object of the present invention is to provide a *Bifidobacterium longum* CBT BG7 strain suitable for use for promotion of the growth of neonates, infants, young children and growing children.

Another object of the present invention is to provide a nutraceutical composition that can promote the growth of neonates, infants, young children and growing children by promoting the digestion of human milk oligosaccharides, promoting vitamin synthesis and also inhibiting the proliferation of harmful bacteria.

Technical Solution

In order to accomplish the above objects, one aspect of the present invention is directed to the provision of a *Bifidobacterium longum* CBT BG7 Bifidobacterium for promotion of growth, internationally deposited with the Korean Collection for Type Culture (KCTC) of the Korea Research Institute of Bioscience and Biotechnology under accession number KCTC 12200BP.

Another aspect of the present invention is directed to the provision of a nutraceutical composition capable of promoting the growth of infants, young children and growing children, which contains the *Bifidobacterium longum* CBT BG7 strain of the present invention.

Advantageous Effects

The *Bifidobacterium longum* CBT BG7 strain of the present invention exhibits an excellent growth promoting effect by digesting and supplying human milk oligosaccharides, which are difficult to industrially produce in large amounts and are not digested by human enzymes, and also promoting vitamin biosynthesis, inhibiting the proliferation of harmful intestinal bacteria, promoting the growth of beneficial bacteria, and regulating the immune system.

The nutraceutical composition for promotion of growth according to the present invention may promote the growth and development of neonates, infants, young children and growing children by activating metabolisms in balance and regulating the immune system, and may also promote brain development. In addition, the nutraceutical composition for promotion of growth according to the present invention may alleviate growth retardation, development retardation, deterioration of physical strength, and low body weight.

BEST MODE

Figure 1:
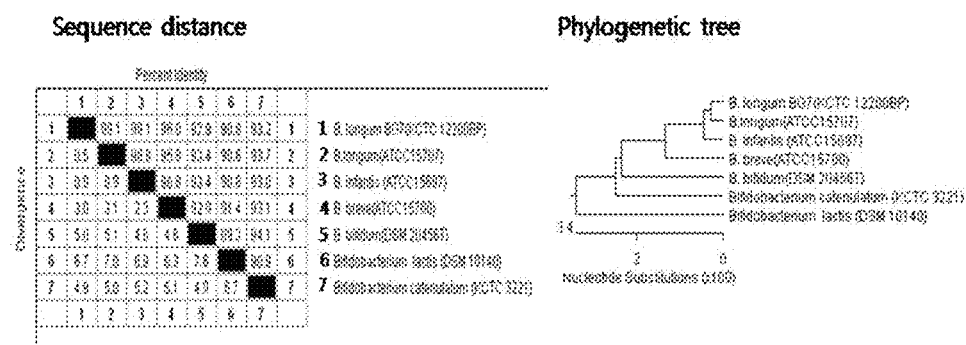
FIG. 1 shows the 16S rRNA gene sequence of a *Bifidobacterium longum* CBT BG7 strain (KCTC 12200BP) according to the present invention (SEQ ID NO: 1), and also shows the comparisons of the 16S rRNA gene sequence homologies and phylogenetic relationships between the *Bifidobacterium longum* CBT BG7 strain of the present invention and related species.

Hereinafter, the present invention will be described in greater detail.

One aspect of the present invention is directed to a *Bifidobacterium longum* CBT BG7 strain, which has an excellent growth promoting effect and was internationally deposited with the Korean Collection for Type Culture (KCTC) of the Korea Research Institute of Bioscience and Biotechnology under accession number KCTC 12200BP.

The *Bifidobacterium longum* CBT BG7 strain according to the present invention can promote the growth and development of neonates, infants and growing children by digesting human milk oligosaccharides (HMOs), which are not digested by human enzymes and are difficult to industrially produce in large amounts due to their very complex structure, and supplying human milk oligosaccharides to infants or young children who take this strain, and also producing metabolites such as vitamins that can function as nutrients in the human body.

It is known that human milk contains 200 or more kinds of oligosaccharides having useful functions. It is known that human milk oligosaccharides promote the proliferation and propagation of beneficial intestinal microbial flora, inhibit the proliferation of harmful bacteria, function as regulator of cell responses, regulate the immune system, and contribute to the brain development of neonates and infants by supplying brain activity energy as a component essential for the brain growth and development of neonates and infants.

The human milk oligosaccharides have resistance to enzymatic digestion in the upper gastrointestinal tract and in the small intestines, and thus reach the colon without being damaged and function as a substrate for fermentation in the colon. It is thought that human milk contains several factors that promote the proliferation of beneficial intestinal microbial flora that inhibit the proliferation of pathogenic microorganisms. A process of enabling human milk oligosaccharides to increase the number of beneficial bacteria and reduce the number of potentially pathogenic bacteria occurs through competition for cell surface receptors, competition for essential nutrients, production of antibacterial agents, and production of inhibitory compounds such as single-chain fatty acids (SCFAs), which can lower the pH of excrement and inhibit potentially pathogenic bacteria. Human milk oligosaccharides are fermented to produce SCFAs such as acetic acid, propionic acid and butyric acid. It is thought that such SCFAs contribute to calories, function as a major energy source for the intestinal epithelium, stimulate the absorption of sodium and water in the colon, and enhance digestion and absorption in the small intestines. In addition, SCFAs contribute to general gastrointestinal health by regulating gastrointestinal development and immune functions.

Human milk oligosaccharides (HMOs) are composed of various oligosaccharides, mainly five monosaccharides: D-glucose (Glc), D-galactose (Gal), N-acetylglucosamine (GlcNAc), L-fucose (Fuc), and sialic acid (Sia; N-acetylneuraminic acid [Neu5Ac]).

The genome of the *Bifidobacterium longum* CBT BG7 strain according to the present invention includes various kinds of genes encoding enzymes that digest human milk oligosaccharides (HMOs), such as α-mannosidase that hydrolyzes α-mannose, β-galactosidase that hydrolyzes β-galactose, and endo-α-N-acetylglucosaminidase that hydrolyzes α-mannosidase and the α bond of galactosyl-β-1,3-N-acetyl-galactosmine of the serine and threonine residues of mucin and mucin-type glycoproteins.

In addition, the genome of the *Bifidobacterium longum* CBT BG7 strain according to the present invention can synthesize nicotinic acid (B3) among vitamins of group B from L-aspartate.

According to another aspect of the present invention, the *Bifidobacterium longum* CBT BG7 strain of the present invention may be used as probiotic Bifidobacteria or may be used in various milk products and other fermentation products.

Still another aspect of the present invention is directed to a nutraceutical composition for promotion of growth, which contains the *Bifidobacterium longum* CBT BG7 strain of the present invention. Currently, human milk oligosaccharides (HMOs) cannot be produced in large amounts or are not commercially available, and thus are not contained in most formula milk or formula food products. Although human milk oligosaccharides (HMOs) are essential nutrient sources for infants, these oligosaccharides are not digested by human enzymes, and are excreted as feces if these are not digested. The nutraceutical composition for promotion of growth according to the present invention can promote the brain development and growth of neonates and infants by digesting and supplying human milk oligosaccharides. The food composition is a food, a supplement, a probiotic or a symbiotic. The term "probiotic" used herein refers to live microorganisms that are beneficial for the health of the host organism when they are supplied in suitable amounts. The term "symbiotic" used herein refers to foods containing a mixture of a prebiotic and a probiotic.

In some embodiments, the composition of the present invention may further contain, in addition to the *Bifidobacterium longum* CBT BG7 strain, one or more lactic acid bacteria or Bifidobacteria strains selected from the group consisting of *Lactobacillus salivarius, Lactobacillus brevis, Lactobacillus helveticus, Lactobacillus fermentum, Lactobacillus paracasei, Lactobacillus casei, Lactobacillus delbrueckii, Lactobacillus reuteri, Lactobacillus buchneri, Lactobacillus gasseri, Lactobacillus johonsonii, Lactobacillus kefir, Lactococcus lactis, Bifidobacterium bifidum, Bifidobacterium pseudolongum, Bifidobacterium themophilum,* and *Bifidobacterium adolescentis.*

The *Bifidobacterium longum* CBT BG7 strain according to the present invention can be proliferated by culture in a medium that is generally used for culture of Bifidobacteria, and can be recovered after culture. The culture product obtained after culture may be used intact, and, if required, may be subjected to crude purification using centrifugation and/or solid-liquid separation using filtration or a sterilization operation. Preferably, only the Bifidobacteria cells are recovered by centrifugation. In addition, the Bifidobacteria that are used in the present invention may be wet cells or dry cells. For example, the Bifidobacteria may be formulated as a probiotic by lyophilization and used in that state.

The composition of the present invention may further contain, in addition to the *Bifidobacterium longum* CBT BG7 strain, a conventional carrier or excipient. In addition, the composition of the present invention may be formulated with various additives such as binders, disintegrants, coating agents, lubricants and the like.

The composition of the present invention may be formulated in the form of powders, granules, tablets or liquids by mixing the *Bifidobacterium longum* CBT BG7 STRAIN with a suitable carrier, excipient, other active ingredients, etc. In addition, the strain of the present invention may be enteric coated using a known method so that the active ingredient Bifidobacteria will reach the colon after passage through the gastrointestinal tract and will be rapidly released in the intestines.

Excipients that may be used in the present invention include saccharides such as sucrose, lactose, mannitol or glucose, and starches such as corn starch, potato starch or partially pre-gelatinized starch. Binders that may be used in the present invention include polysaccharides such as dextrin, sodium alginate, carrageenan gum, guar gum, acacia gum, agar and the like; naturally occurring macromolecular substances such as tragacanth gum, gelatin, gluten and the like; cellulose derivatives such as hydroxypropyl cellulose, methyl cellulose, hydroxypropylmethyl cellulose, ethyl cellulose, hydroxypropylethyl cellulose, carboxymethyl cellulose and the like; and polymers such as polyvinylpyrrolidone, polyvinyl alcohol, polyvinyl acetate, polyethylene glycol, polyacrylic acid, polymethacrylic acid and vinyl acetate resins.

Disintegrants that may be used in the present invention include cellulose derivatives such as carboxymethylcellulose, carboxymethylcellulose calcium, low-substituted hydroxypropyl cellulose, etc.; and starches such as sodium carboxymethyl starch, hydroxypropyl starch, corn starch, potato starch, rice starch and partially pre-gelatinized starch.

Examples of lubricants that may be used in the present invention include talc, stearic acid, calcium stearate, magnesium stearate, colloidal silica, hydrous silicon dioxide, various kinds of waxes and oils, etc.

Coating agents that may be used in the present invention include water-insoluble polymers such as dimethylaminoethylmethacryklate-methacrylic acid copolymers, polyvinylacetaldiethylaminoacetate, ethylacrylate-methacrylic acid copolymers, ethylacrylate-methylmethacrylate-chlorotrimethyl ammonium ethylmethacrylate copolymers, ethylcellulose, etc.; enteric polymers such as methacrylic acid-ethylacrylate copolymers, hydroxypropylmethylcellulose phthalate, hydroxypropylmethylcellulose acetate succinate, etc.; and water-soluble polymers such as methylcellulose, hydroxypropyl methylcellulose, polyvinylpyrrolidone, polyethylene glycol, etc., but are not necessarily limited thereto.

The content of the active ingredient *Bifidobacterium longum* CBT BG7 strain in the composition for promotion of growth according to the present invention can be suitably determined in view of the subject's weight, age or sex. For example, the composition of the present invention contains, as an active ingredient, the *Bifidobacterium longum* CBT BG7 strain at a nutritionally effective concentration relative to the total weight of the composition. Preferably, the composition contains the *Bifidobacterium longum* CBT BG7 strain in an amount of $10^8$ to $10^{12}$ cfu/g or contains a culture product having the same number of live bacteria. Generally, for adults, $1 \times 10^6$ or more live bacteria, preferably $1 \times 10^8$ to $1 \times 10^{12}$ live bacteria, may be taken once or several times as needed.

In still another aspect, the nutraceutical composition for promotion of growth according to the present invention may further contain one or more other prebiotics selected from the group consisting of *Bifidobacterium longum* bv. *infantis* CBT BT1 (KCTC 11859BP), *Bifidobacterium breve* CBT BR3 (KCTC 12201BP), and *Bifidobacterium bifidum* CBT BF3 (KCTC 12199BP). This composition may contain each Bifidobacterium strain at the same percentage.

Hereinafter, the present invention will be described with reference to examples. It is to be understood, however, that these examples are only for illustrative purposes and are not intended to limit the scope of the present invention.

EXAMPLES

Example 1: Isolation and Identification of *Bifidobacterium longum* CBT BG7 Strain 1-1: Selection of Novel Strain 1 g of human feces was serially diluted in sterile anaerobic water, and 1 ml of each of the dilutions was poured on glucose blood liver (BL. BD. USA) solid medium and cultured for 3 days under anaerobic conditions. The produced colonies were selected using a Bifidobacterium selective medium obtained by adding BCP (Bromocresol purple, 0.17 g/L) to BL, and then cultured for 3 days under the same conditions. Bifidobacterium colonies, the color around which changed to yellow, were selected, and then biochemical and molecular biological identification of the selected colonies was performed. Thereafter, one strain having the best physical properties was selected.

1-2: Identification of Selected Strain

1) Analysis of Sugar Utilization

The sugar utilization of the strain isolated from human feces was examined using an API 50 CHL kit. The results obtained by examining the sugar utilization were analyzed using the API web (https://apiweb.biomerieux.com), and the results of the analysis are shown in Table 1 below:

TABLE 1

| No. | Carbohydrates | Utilized |
|---|---|---|
| 0 | Control | − |
| 1 | Glycerol | − |
| 2 | Erythritol | − |
| 3 | D-Arabinose | − |
| 4 | L-Arabinose | + |
| 5 | Ribose | + |
| 6 | D-Xylose | + |
| 7 | L-Xylose | − |
| 8 | Adonitol | − |
| 9 | β-Methyl-xyloside | − |
| 10 | Galactose | + |
| 11 | D-Glucose | + |
| 12 | D-Fructose | + |
| 13 | D-Mannose | + |
| 14 | L-Sorbose | − |
| 15 | Rhamnose | − |
| 16 | Dulcitol | − |
| 17 | Inositol | − |

TABLE 1-continued

| No. | Carbohydrates | Utilized |
|---|---|---|
| 18 | Mannitol | + |
| 19 | Sorbitol | + |
| 20 | α-Methyl-D-mannoside | − |
| 21 | α-Methyl-D-glucoside | + |
| 22 | N-Acetyl glucosamine | − |
| 23 | Amygdaline | − |
| 24 | Arbutine | + |
| 25 | Esculine | + |
| 26 | Salicine | + |
| 27 | Cellobiose | − |
| 28 | Maltose | + |
| 29 | Lactose | + |
| 30 | Melibiose | + |
| 31 | Saccharose | + |
| 32 | Trehalose | − |
| 33 | Inuline | − |
| 34 | Melezitose | − |
| 35 | D-Raffinose | + |
| 36 | Amidon | − |
| 37 | Glycogene | − |
| 38 | Xylitol | − |
| 39 | β-Gentiobiose | − |
| 40 | D-Turanose | w |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Gluconate | − |
| 48 | 2-Ceto-gluconate | − |
| 49 | 5-Ceto-gluconate | w |

2) 16s rRNA Identification

In order to identify the selected strain using a molecular biological method, the 16s rRNA gene sequence of the strain was analyzed. Genomic DNA was extracted from 1 ml of the pure culture of the strain (isolated from feces) by use of an Accuprep genomic extraction kit (Bioneer, Korea). Using the extracted DNA as a template, the 16s gene rRNA region was amplified by PCR (MyCycler, BIO-RAD, USA) using primer F (5'-AGAGTTTGATCCTGGCTCAG-3') and primer R (5'-AAGGAGGTGATCCAGCC-3'). The PCR product was ligated to a pGEM-Teasy vector (Promega, USA) and transformed into an *E. coli* DH5α strain, after which it was plated on an LB/x-gal/amp plate and cultured overnight at 37° C. A recombinant plasmid containing the insert was isolated from the transformant by screening, followed by DNA sequencing. In the DNA sequencing, the homology of the isolated strain to various *Bifidobacterium* sp. strains, including *B. longum$^T$* (ATCC 15707), was analyzed using the Cluster V method of DNA star program. As shown in FIG. 1, the 16s rRNA gene sequence of the isolated strain showed a homology of 99.1% to *B. longum$^T$* (ATCC 15707).

3) RAPD (Random Amplified Polymorphic DNA) Analysis

For RAPD analysis, genomic DNA was extracted from the *Bifidobacterium longum* CBT BG7 strain isolated from feces. Using the isolated DNA as a template, PCR-RAPD (MyCycler, BIO-RAD, USA) was performed using a $(GTG)_5$ (5'-GTGGTGGTGGTGGTG-3') primer. The resulting PCR product was stained with EtBr, and then observed with G:BOX (SYNGENE, UK). In addition, in the PFGE analysis, the purely cultured *Bifidobacterium longum* CBT BG7 strain was adjusted to a final OD of $OD_{600}$=4 to construct a plug. Then, the genomic DNA was digested using various enzymes and subjected to electrophoresis, after which it was analyzed comparatively with the control *B. longum$^T$* (ATCC 15707).

Figure 2:
FIG. 2 shows the results of RAPD (Random Amplified Polymorphic DNA) analysis of the genomic DNA of the *Bifidobacterium longum* CBT BG7 strain according to the present invention.

As can be seen in FIG. 2, the result of RAPD indicated that the *Bifidobacterium longum* CBT BG7 strain showed a band pattern different from that of *B. longum$^T$* (ATCC 15707). In FIG. 2, lane 1 indicates the result for *B. longum$^T$* (ATCC 15707), and lane 2 indicates the result for *Bifidobacterium longum* CBT BG7. Based on the above results, it was found that the microorganism *Bifidobacterium longum* CBT BG7 isolated from feces was a novel strain different from *B. longum$^T$* (ATCC 15707).

4) PFGE (Pulsed Field Gel Electrophoresis) Analysis

The O.D. of *Bifidobacterium longum* CBT BG7 purely cultured in BL broth was measured, and then adjusted to a final O.D. of $O.D_{600}$=4 using 2% low melting agarose, thereby constructing a plug. Then, the genomic DNA was digested using various enzymes and subjected to electrophoresis, after which it was analyzed comparatively with the control *B. longum$^T$* (ATCC 15707).

The constructed plug was placed in 1 ml of lysozyme buffer (2 mg/ml Lysozyme (Sigma), 0.05% N-lauorylsarcosine (Sigma)), and 10 μl of 4 mg/ml lysostaphin (Sigma) was added thereto, followed by incubation overnight at 37° C. The plug was carefully taken out and was added to 4 ml of NDS buffer (1 ml 1 M Tris-HCl (pH=8.0), 10 ml 100% SDS, 89 ml 0.5 M EDTA (pH=8.5)), followed by incubation overnight at 50° C. Next, the plug was washed six times with 10 ml of 50 mM EDTA (pH 8.5) with mild shaking, and then was carefully transferred to 400 μl of an enzyme buffer to be treated, followed by incubation at room temperature for 30 minutes. Each plug was transferred to 400 μl of fresh enzyme buffer and a restriction enzyme (20 U) was added thereto, followed by incubation overnight at 37° C. As the restriction enzyme, XbaI and ApaI were used. Electrophoresis was performed using a CHEF system (BIO-RAD, USA) in 0.5× TBE at 5.3 cm/V and a pulse time of 1 s to 15 s for 18 hours.

Figure 3:
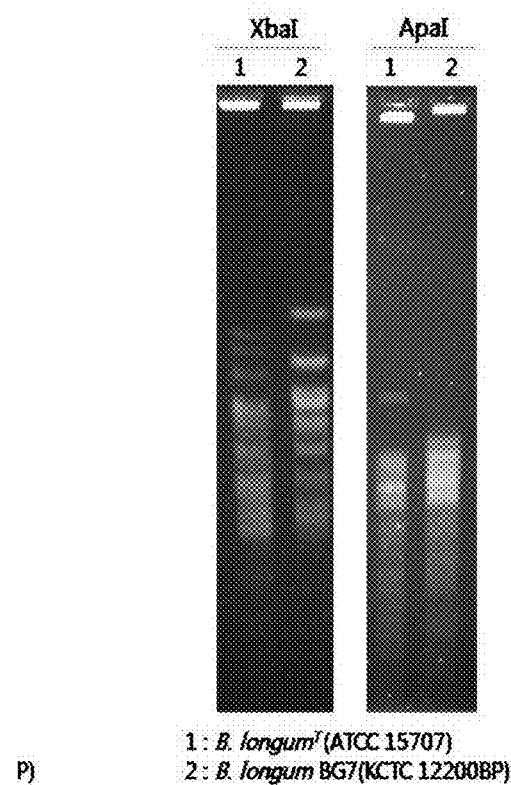
FIG. 3 shows the results of PFGE (Pulsed Field Gel Electrophoresis) analysis of the genomic DNA of the *Bifidobacterium longum* CBT BG7 strain (KCTC 12200BP) according to the present invention.
Figure 4:
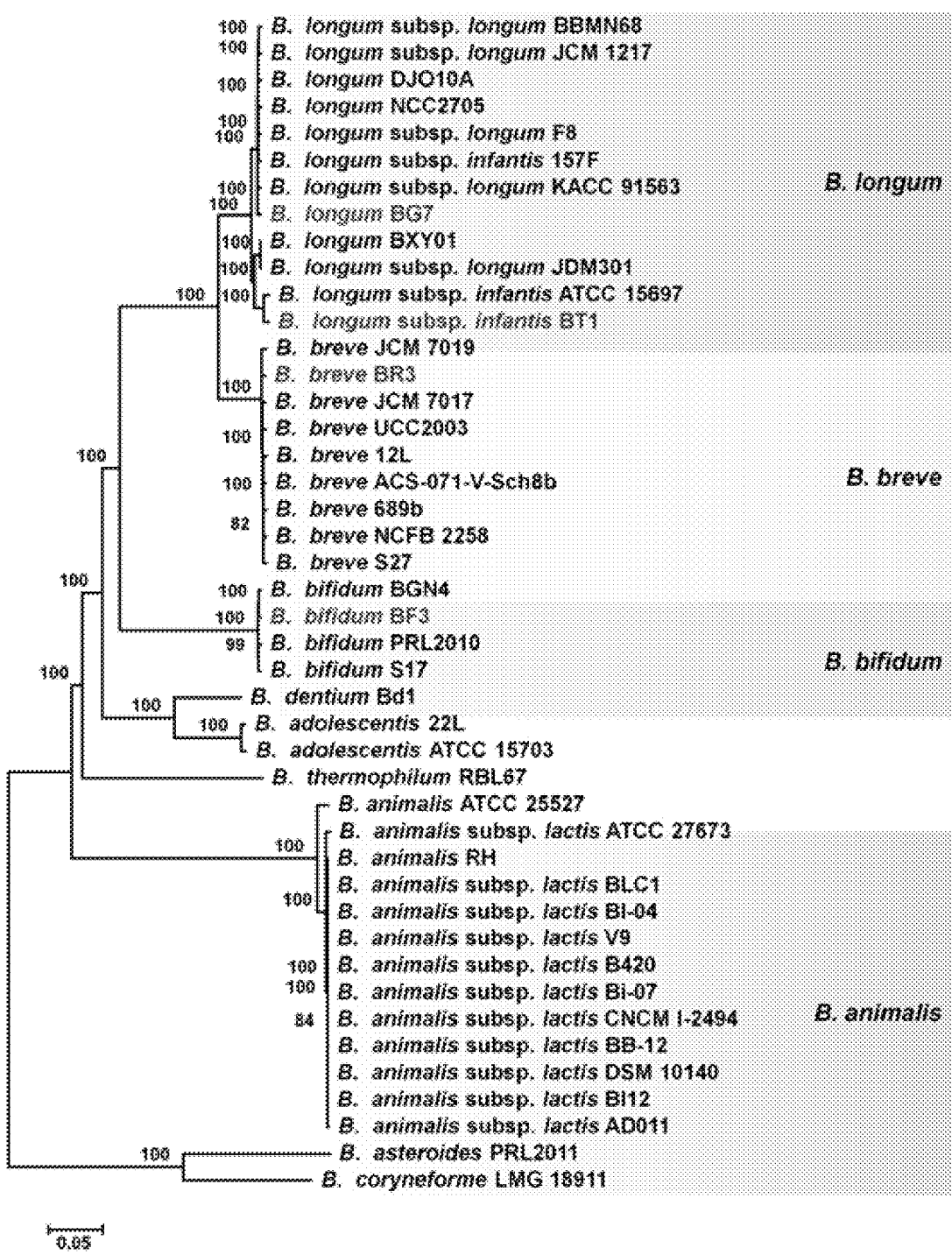
FIG. 4 shows a phylogenetic tree of the *Bifidobacterium longum* CBT BG7 strain of the present invention and related Bifidobacterium species.

After completion of electrophoresis, the plug was stained with EtBr solution, and the band pattern thereof was observed with G:BOX (SYNGENE, UK). The results of the PFGE performed using XbaI and ApaI indicated that *Bifidobacterium longum* CBT BG7 isolated from feces was a novel strain showing a band pattern different from that of *B. longum$^T$* (ATCC 15707). In FIG. 3, lane 1 indicates the result for *B. longum$^T$* (ATCC 15707), and lane 2 indicates the result for *Bifidobacterium longum* CBT BG7.

5) Enzymatic Activity Test

To measure the enzymatic activity of *B. longum* CBT BG7, the difference in enzymes was examined using an API ZYM kit. When the enzymatic activity of *Bifidobacterium longum* CBT BG7 was compared with the enzymatic activity of *B. longum$^T$* (ATCC 15707), *Bifidobacterium longum* CBT BG7 showed an enzymatic activity almost similar to that of *B. longum$^T$* (ATCC 15707). In particular, *Bifidobacterium longum* CBT BG7 showed β-glucosidase activity which was not shown in *B. longum$^T$* (ATCC 15707), and this enzyme functions to degrade glucose contained in peptidoglycans of the cell walls of gram-negative pathogenic strains to thereby inhibit the growth of the pathogenic strains. In addition, *Bifidobacterium longum* CBT BG7 did not show the activity of β-glucuronidase that was a carcinogenic enzyme.

TABLE 2

| Enzyme | B. longum CBT BG7 (KCTC 12200BP) | B. longum (ATCC15707) |
|---|---|---|
| 1. Control | 0 | 0 |
| 2. Alkaline phosphatase | 0 | 0 |
| 3. Esterase (C4) | 2 | 3 |
| 4. Esterase Lipase (C8) | 2 | 2 |
| 5. Lipase (C14) | 0 | 0 |
| 6. Leucine arylamidase | 5 | 5 |
| 7. Valine arylamidase | 0 | 0 |
| 8. Crystine arylamidase | 0 | 0 |
| 9. Trypsin | 0 | 0 |
| 10. α-Chymotrypsin | 0 | 0 |
| 11. Acid phosphatase | 1 | 2 |
| 12. Naphol-AS-BI-phosphohydrolase | 1 | 1 |
| 13. α-Galactosidase | 5 | 5 |
| 14. β-Galactosidase | 5 | 5 |
| 15. β-Glucuronidase | 0 | 1 |
| 16. α-Glucosidase | 5 | 5 |
| 17. β-Glucosidase | 5 | 0 |
| 18. N-Acetyl-p-glucosidase | 1 | 1 |
| 19. α-Mannosidase | 1 | 0 |
| 20. α-Fucosidase | 0 | 0 |

0, 0 nmol;
1, 5 nmol;
2, 10 nmol;
3, 20 nmol;
4, 30 nmol;
5, ≥40 nmol.

6) Other Mycological Characteristics

The characteristics of *Bifidobacterium longum* CBT BG7 according to the present invention are as follows:

TABLE 3

1) Morphology of bacteria

The characteristics of the bacteria cultured in MRS agar plate medium at 37° C. for 2 days.
① type of cells: *bacillus*
② mobility: none
③ spore forming ability: none
④ gram staining: positive 2) Morphology of colony The morphology of the colony cultured in MRS agar plate medium at 37° C. for 2 days.
① shape: circular
② raised: convex
③ surface: smooth 3) Physiological properties ① growth temperature: viable growth temperature: 15 to 40° C.
optimum growth temperature: 37° C.
② growth pH: viable growth pH: 5.0-7.5
optimum pH: 6.0-6.5
③ Influence of oxygen: anaerobic 4) Catalase  −
5) Formation of gas  −
6) Growth at 15° C.  −
7) Growth at 45° C.  +
8) Production of indole  −
9) Production of lactic acid  +

Based on the above-described results, the isolated strain was named "*Bifidobacterium longum* CBT BG7" strain, deposited with the Korean Collection for Type Culture (KCTC), which is an international depository authority, on May 7, 2012, and assigned accession number KCTC 12200BP.

1-3: Functionality and Stability

1) Antibiotic Resistance Test

In order to verify the safety of the isolated *Bifidobacterium longum* CBT BG7 strain (KCTC 12200BP), the antibiotic resistance of the isolated strain was analyzed. The antibiotic resistance test was performed using the microdilution method recommended by the European Food Safety Authority (EFSA), and 10 kinds of antibiotics, including ampicillin vancomycin (VAN), gentamicin (GEN), kanamycin (KAN), streptomycin (STM), erythromycin (ERM), quinupristin/dalfopristin (Q/D), clindamycin (CLM), tetracycline (TET) and chloramphenicol (CP), were used in the test.

For the antibiotics excluding clindamycin, each antibiotic was added to a mixture of 10% ISO-sensitest broth and 90% MRS broth at concentrations of 256, 128, 64, 32, 16, 8, 4, 2, 1, 0.5 μg/ml. Clindamycin was added at concentrations of 16, 8, 4, 2, 1, 0.5, 0.25, 0.125, 0.0625 and 0.03125 μg/ml because the EFSA break point value of the lactobacillus group is 0.25 μg/ml or less. In addition, the test for quinupristin/dalfopristin (Q/D) was performed using an E-test strip (BioMeriux).

Microplates were incubated at 37° C. for 48 hours under anaerobic conditions, and then MIC was measured as the minimum antibiotic concentration at which no visible growth was observed.

Based on the EFSA break point, whether *Bifidobacterium longum* CBT BG7 would have resistance to each antibiotic was analyzed, and the results of the analysis are shown in Table 4 below:

TABLE 4

| Strain | AMP | VAN | GEN | KAN | STM | ERM | CLM | Q/D | TET | CP |
|---|---|---|---|---|---|---|---|---|---|---|
| MIC of CBT BG7 | <0.5 | <0.5 | <16 | <256 | <32 | <0.5 | <0.125 | <0.19 | <8 | <2 |
| EFSA break point (μg/L) | 2 | 2 | 64 | nr | 128 | 0.5 | 0.25 | 1 | 8 | 4 |

It was shown that the resistances of the isolated *Bifidobacterium longum* CBT BG7 strain to all the antibiotics used in the test were lower than the EFSA antibiotic resistance standards, indicating that the isolated strain satisfied the stability standards for EFSA antibiotics. Since it was reported that Bifidobacteria have resistance to aminoglycosides such as kanamycin due to the absence of a cytochrome-mediated drug transport system, EFSA does not require the MIC value of the drug for Bifidobacteria.

2) Test for Intestinal Colonization

The measurement of intestinal colonization of *Bifidobacterium longum* CBT BG7 was performed in the HT-29 cell line derived from human colon epithelial cells while *Bifidobacterium longum$^T$* (ATCC 15707) was used as a control. The HT-29 cell line was treated with each of the strains for 1 hour, and gram staining and viable cell counting were performed to compare the intestinal colonization ability between the strains. The results of the measurement are shown in Table 5 below.

TABLE 5

|  | *Bifidobacterium longum* CBT BG7 | *Bifidobacterium longue$^T$* |
|---|---|---|
| Intestinal colonization rate (%) | 92.15 | 83.40 |

The results of measurement of the intestinal colonization indicated that the *Bifidobacterium longum* CBT BG7 strain showed excellent intestinal colonization ability compared to the *Bifidobacterium longum$^T$* (ATCC 15707) strain. Such results suggest that the strain of the present invention can adhere to intestinal epithelial cells to improve the intestinal environment.

3) Acute Toxicity Test

In order to verify the safety of the *Bifidobacterium longum* CBT BG7 strain of the present invention, an acute toxicity test was performed on test animals. The lyophilized strain of the present invention was administered orally to 6-week-old male and female Sprague-Dawley (SD) rats in an amount of $1.0 \times 10^{11}$ cfu/kg. For a control group, 0.85% saline was administered intragastrically. Clinical symptoms in all the test animals were observed once a day for 14 days (a period ranging from 1 day after sample administration to the day of autopsy). The results of the observations are shown in Table 6 below.

After administration of the *Bifidobacterium longum* CBT BG7 strain, no death could be observed in all the control group and the administered group, and an animal showing specific clinical symptoms could not be found. In addition, the intakes of feed and water and the body temperature were observed for 14 days after administration, and, as a result, a statistically significant difference between the administered group and the control group could not be found.

TABLE 6

| Sex | Strain | 1 | 2 | 3 | 4 | 5 | 6 | 7 | 8 | 9 | 10 | 11 | 12 | 13 | 14 | Death rate (%) | $LD_{50}$ |
|---|---|---|---|---|---|---|---|---|---|---|---|---|---|---|---|---|---|
| | | Days after administration | | | | | | | | | | | | | | | |
| Male | CBT BG7 | 0 | 0 | 0 | 0 | 0 | 0 | 0 | 0 | 0 | 0 | 0 | 0 | 0 | 0 | 0 | >$10^{11}$ cfu/kg |
| | Control | 0 | 0 | 0 | 0 | 0 | 0 | 0 | 0 | 0 | 0 | 0 | 0 | 0 | 0 | 0 | |
| Female | CBT BG7 | 0 | 0 | 0 | 0 | 0 | 0 | 0 | 0 | 0 | 0 | 0 | 0 | 0 | 0 | 0 | >$10^{11}$ cfu/kg |
| | Control | 0 | 0 | 0 | 0 | 0 | 0 | 0 | 0 | 0 | 0 | 0 | 0 | 0 | 0 | 0 | |

\* The numeral in Table 6 indicates the number of dead animals.

Example 2: Analysis of Genes of *Bifidobacterium longum* CBT BG7 Strain

Genome sequencing of the *Bifidobacterium longum* CBT BG7 strain (KCTC 12200BP) was performed using a PacBio RS II System (DNA Link, Republic of Korea). For the genome of the strain, a 10-kb library was constructed, and genome sequencing was performed using one of SMRT cells with C2-P4 chemistry. By the genome sequencing, a sequence having a length of 337,655,282 bp was obtained. De novo assembly was performed using SMRTpipe HGAP, and scaffolding and gap filling were performed using SMRTpipe AHA. Prediction of structural genes was performed using Glimmer3, and gene annotation was performed by AutoFACT (Koski et al. 2005) using the results obtained by BLASTP for Pfam, Uniref100, KEGG, COG and GenBank NR databases. Transfer RNA and ribosomal RNA were performed using tRNAscan-SE (Lowe and Eddy 1997) and RNAmmer (Lagesen et al. 2007), respectively. The functional classification of genes by Clusters of Orthologous Groups (COGs) category was performed using RPS-BLAST at an e-value cutoff of less than 1e-2 (Mavromatis et al. 2009).

The presence of specific genes on the genome was determined using BLASTP with a parameter of sequence homology ≥50% for a collected data set. Metabolic pathway analysis of the genome was performed using a KEGG automatic annotation server (Moriya et al. 2007). Analysis of secondary metabolite biosynthetic genes was performed using antiSMASH version 3.0.0 (Blin et al. 2013; Blin et al. 2014) (http://antismash.secondarymetabolites.org/).

2-1: HMO (Human Milk Oligosaccharide) Metabolism-Related Genes

Figure 5:
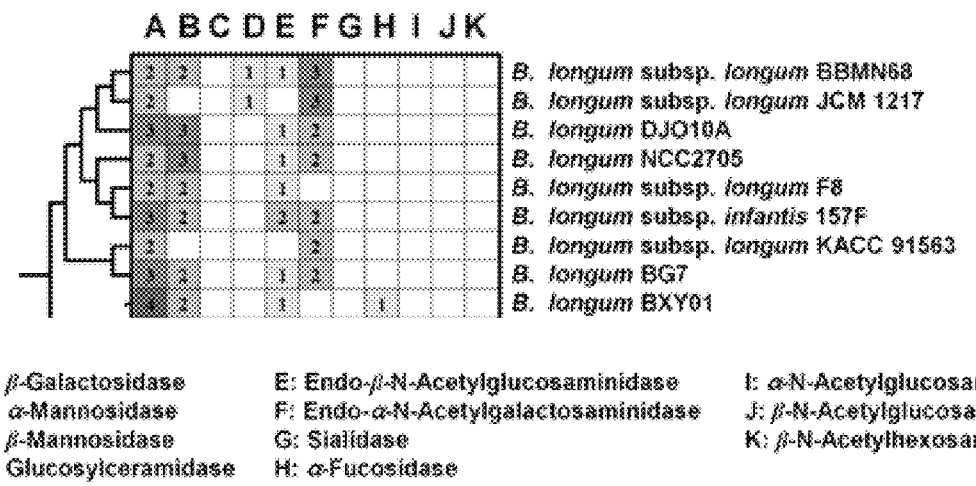
FIG. 5 shows the number of human milk oligosaccharide metabolism-related genes of the *Bifidobacterium longum* CBT BG7 strain according to the present invention.

The gene contents of the genome of the *Bifidobacterium longum* CBT BG7 strain according to the present invention were analyzed. As a result of this analysis, it was found that the genome of the strain contained genes that encoded β-galactosidase, α-mannosidase and endo-α-N-acetylgalactosaminidase, among human milk oligosaccharide metabolism-related genes. This suggests that the strain of the present invention can digest and supply human milk oligosaccharides that are not digested by human enzymes (see FIG. 5).

TABLE 7

| Strain | Enzyme | Accession number |
|---|---|---|
| B. longum CBT BG7 | Beta-galactosidase | RY68_0416 |
| B. longum CBT BG7 | Beta-galactosidase | RY68_0534 |
| B. longum CBT BG7 | Beta-galactosidase | RY68_0735 |
| B. longum CBT BG7 | Alpha-mannosidase | RY68_1335 |
| B. longum CBT BG7 | Alpha-mannosidase | RY68_1336 |
| B. longum CBT BG7 | Endo-beta-N-acetylglucosaminidase | RY68_1329 |
| B. longum CBT BG7 | Endo-alpha-N-acetylgalactosaminidase | RY68_0178 |
| B. longum CBT BG7 | Endo-alpha-N-acetylgalactosaminidase | RY68_1842 |

2-2: Vitamin Biosynthetic Genes

The results of the gene analysis indicated that the *Bifidobacterium longum* CBT BG7 strain of the present invention had a gene that biosynthesized nicotinate (B3) among vitamins of group B from L-aspartate.

TABLE 8

| | Folate (B9) [a] | Folate (B9) [b] | Nicotinate (B3) | Riboflavin (B2) |
|---|---|---|---|---|
| B. longum subsp. longum BBMN68 | — | — | ○ | — |
| B. longum subsp. longum JCM 1217 | — | — | ○ | — |
| B. longum DJO10A | — | — | ○ | — |
| B. longum NCC2705 | — | — | ○ | — |
| B. longum F8 | — | — | ○ | — |
| B. longum subsp. infantis 157F | — | — | ○ | — |
| B. longum subsp. longum KACC 91563 | — | — | ○ | — |
| B. longum CBT BG7 | — | — | ○ | — |
| B. longum BXY01 | ○ | ○ | ○ | ○ |

[a] Folate from GTP;
[b] Formateformchorismate

TABLE 9

| Nicotinate biosynthetic genes from L-aspartate | | | |
|---|---|---|---|
| KO number | K00278 | K03517 | K00767 | K00763 |
| EC number | 1.4.3.16 | 2.5.1.72 | 2.4.2.19 | 6.3.4.21 |
| B. longum CBT BG7 | RY68_1286 | RY68_1287 | RY68_1285 | RY68_0390 |

2-3: Inhibition of Growth of Harmful Bacteria

In order to examine whether the strain of the present invention had the effect of inhibiting the growth of harmful bacteria by producing antibiotics, whether secondary metabolite biosynthetic genes and antibiotic production-related genes were present in the genome of the *Bifidobacterium longum* CBT BG7 strain was analyzed.

Figure 6:
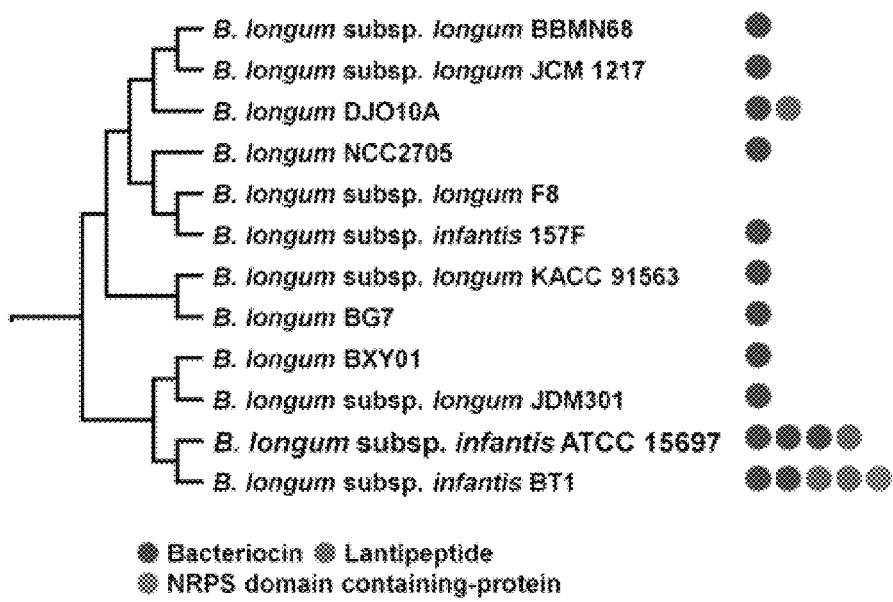
FIG. 6 shows whether the secondary metabolite biosynthetic genes are present in the *Bifidobacterium longum* CBT BG7 strain of the present invention.

Biosynthesis of secondary metabolites was examined. As a result, as can be seen in FIG. 6, it was found that the *Bifidobacterium longum* CBT BG7 strain of the present invention included a gene that encoded bacteriocin. From these results, it can be seen that the *Bifidobacterium longum* CBT BG7 strain of the present invention can inhibit the proliferation of pathogenic bacteria by producing antibiotic compounds such as bacteriocin.

2-4: Absence of Pathogenic Gene

Analysis of PAIs (pathogenicity islands) and REIs (antimicrobial resistance islands) was performed using the PAI finder of the PAI database (Yoon et al. 2007; Yoon et al. 2015). The results of the analysis indicated that PAI (pathogenicity islands) and a PAI-like region are not present in the genome of the *Bifidobacterium longum* CBT BG7 strain of the present invention.

Example 3: Growth Promoting Effect of *Bifidobacterium longum* CBT BG7 Strain

The following Example demonstrates the characteristics and growth promoting effect of the strain of the present invention. All the experimental results obtained in the Example were expressed as mean±SD, and statistical processing of the experimental results was performed using GraphPad Prism™ 6.0. In addition, the significance of difference in means between the test groups was determined by one-way ANOVA, and then the Post Hoc test was performed using Tukey's multiple range test.

3-1: Preparation of Culture of Strain of the Present Invention and Composition Containing the Same The *Bifidobacterium longum* CBT BG7 strain (KCTC 12200BP) was cultured in BL broth (BD Diagnostics, Sparks, Md.) at 37° C. for 24 hours, and diluted to $10^{11}$ CFU/ml in phosphate buffered saline (PBS, 10 mM sodium phosphate, 130 mM sodium chloride, pH 7.4). The dilution was sonicated and centrifuged to separate the supernatant, followed by filtration through a filter having a pore size of 0.45 μm. The filtrate was freeze-dried, and then stored at −20° C. until use in in vivo experiments.

3-2: Obesity Animal Model and Sampling

Animal tests were carried out in accordance with the Animal use and Care Protocol of the Institutional Animal Care and Use Committee (IACUC). As test animals, 6-week-old SD rats (10 rats per group, consisting of five male rats and five female rats) were purchased from Saeron Bio Inc. (Uiwang, Korea) and acclimated for 24 hours. Then, the rats were raised for 17 days at a temperature of 24+2° C. and a humidity of 55±15% with a 12-hr light/12-hr dark cycle. For elemental diets, the rats were allowed to take barley feed (A04, UAR, Vilemoisson-sur-Orge, France) for 17 days, and were also allowed to take drinking water alone or drinking water containing *Bifidobacterium longum* CBT BG7 ($10^7$ CFU/head/day) freely.

3-3: Growth Promoting Effect of Strain of the Present Invention

In order to observe the growth promoting effect of the *Bifidobacterium longum* CBT BG7 strain of the present invention, the rats were fed with barley feed for 17 days to induce elemental diets, and the body weight and the intake of drinking water and feed were measured each day until day 17 after the start of the experiment. The gain in the body weight was calculated by subtracting the body weight on the day of start of the experiment from the body weight on the day of measurement. The intake of each of drinking water and feed was calculated as the total intake until day 17 by measuring the intake for each cage and then calculating the intake for each rat. The efficiency of the gain in the body weight was calculated by dividing the gain in the body weight by the total intake of feed.

Figure 7:
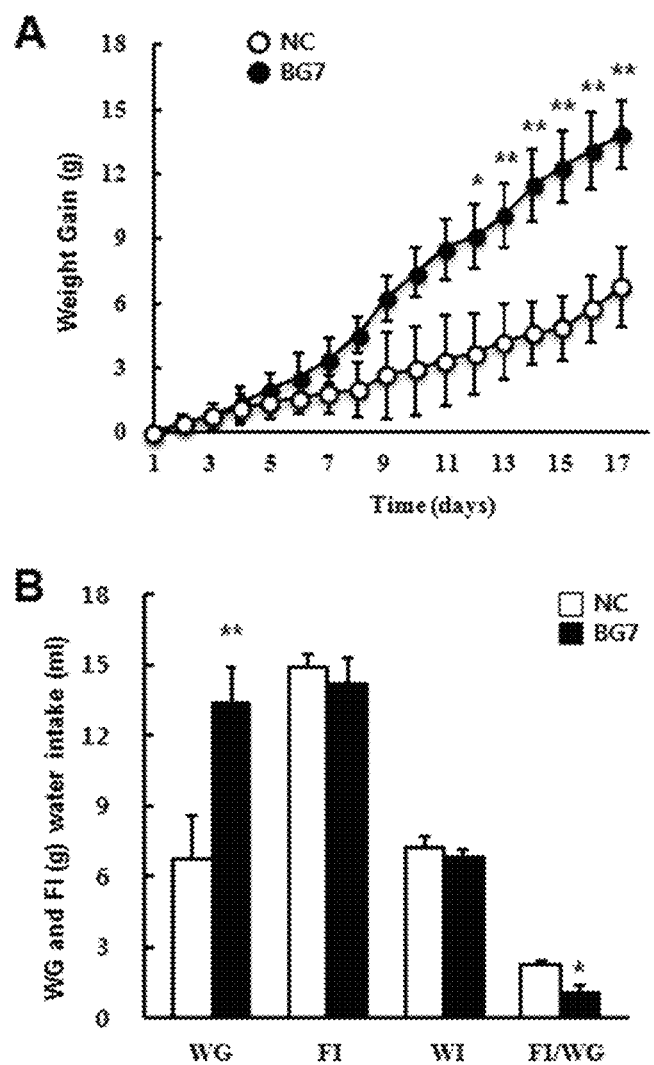
FIG. 7 is a graph showing the growth promoting effect of the *Bifidobacterium longum* CBT BG7 strain of the present invention on mouse growth.

Referring to FIG. 7, it was observed that, in the case of the group (CBT BG7) fed with drinking water containing *Bifidobacterium longum* CBT BG7, the body weight significantly increased from day 9 compared to that of the group (NC) normally fed with general drinking water (12 days; $p<0.05$, 13 to 17 days; $p<0.01$) (FIG. 7(A)). However, the total intake of feed (FI) for 17 days and the total intake of drinking water (WI) for 17 days showed no significant difference between the two groups (FIG. 7(B)). It can be seen that administration of the strain of the present invention did not influence the feed intake and that the weight gain (WG) was not attributable to the difference in the feed intake (FI). The ratio of weight gain to intake of feed (WG/FI) was more significant in the *Bifidobacterium longum* CBT BG7-fed group than in the normal group, indicating that the growth of the rats was promoted by administration of the *Bifidobacterium longum* CBT BG7 strain of the present invention.

The present invention has been described with a focus on the preferred embodiments thereof. Those having ordinary knowledge in the art to which the present invention pertains will appreciate that the present invention may be embodied in various modified or changed forms without departing from the essential features of the present invention. Therefore, the true range of protection of the present invention should be defined by the attached claims and equivalents thereto rather than by the above-described embodiments.

Budapest Treaty on the International Recognition of the Deposit of Microorganisms for the Purposes of Patent Procedure

Receipt in the Case of an Original Deposit issued pursuant to Rule 7.1 by the International Depositary Authority

To: Myung-Jun, Jung

134, Gaegok-ri, Wolgot-myeon, Gimpo-si

Gyeonggi-do 415-872, Republic of Korea

| I. Identification of Microorganism | |
|---|---|
| Identification reference given by the Depositor: *Bifidobacterium longum infantis* BT(1) | Accession number given by the International Depositary Authority: KCTC 11859BP |
| II. Scientific Description and/or Proposed Taxonomic Designation ||
| The microorganism identified under I above was accompanied by: <br> [X] a scientific description <br> [ ] a proposed taxonomic designation <br> (Mark with a cross where applicable) ||
| III. Receipt and Acceptance ||
| This International Depository Authority accepts the microorganism identified under I above, which was received by it on February 17, 2011. ||
| IV. Receipt for Request of Conversion ||
| The microorganism identified under I above was received by this International Depositary Authority on __, and a request to convert the original deposit to a deposit under the Budapest Treaty was received by it on __. ||
| V. International Depository Authority ||
| Name: Biological Resource Center <br> Address: Korea Research Institute of Bioscience and Biotechnology <br> 125, Gwahak-ro, Yuseong-gu, Daejeon <br> 305-806, Republic of Korea | Signature of a person having the power to represent the International Depositary Authority: <br> Director: Jung-Sook, Lee <br> Date: March 2, 2011 |

Budapest Treaty on the International Recognition of the Deposit of Microorganisms for the Purposes of Patent Procedure

Attestation Concerning the Later Indication or an Amendment of the Scientific Description and/or Proposed Taxonomic Designation pursuant to Rule 8.2

To: Myung-Jun, Jung

134, Gaegok-ri, Wolgot-myeon, Gimpo-si

Gyeonggi-do 415-872, Republic of Korea

| The enclosed communication has been received by the International Depository Authority on February 17, 2011.<br><br>KCTC 11859BP<br>*Bifidobacterium longum* bv. *infantis* BT(1) → *Bifidobacterium longum infantis* CBT BT1 ||
| International Depository Authority ||
| Name: Biological Resource Center<br>Address: Korea Research Institute of Bioscience and Biotechnology<br>125, Gwahak-ro, Yuseong-gu, Daejeon 305-806, Republic of Korea | Signature of a person having the power to represent the International Depository Authority:<br>Director: Doo-Sang, Park<br>Date: May 7, 2015 |

Enclosure: Communication of the later indication or an amendment of the scientific description and/or taxonomic designation pursuant to Rule 8.1.

Budapest Treaty on the International Recognition of the Deposit of Microorganisms for the Purposes of Patent Procedure

Receipt in the Case of an Original Deposit issued pursuant to Rule 7.1 by the International Depositary Authority

To: Myung-Jun, Jung

134, Gaegok-ri, Wolgot-myeon, Gimpo-si,

Gyeonggi-do 415-872, Republic of Korea

| I. Identification of Microorganism ||
|---|---|
| Identification reference given by the Depositor: *Bifidobacterium breve* BR3 | Accession number given by the International Depositary Authority: KCTC 12201BP |
| II. Scientific Description and/or Proposed Taxonomic Designation ||
| The microorganism identified under I above was accompanied by: <br> [X] a scientific description <br> [ ] a proposed taxonomic designation <br> (Mark with a cross where applicable) ||
| III. Receipt and Acceptance ||
| This International Depository Authority accepts the microorganism identified under I above, which was received by it on April 27, 2012. ||
| IV. Receipt for Request of Conversion ||
| The microorganism identified under I above was received by this International Depositary Authority on __, and a request to convert the original deposit to a deposit under the Budapest Treaty was received by it on __. ||
| V. International Depository Authority ||
| Name: Biological Resource Center <br> Address: Korea Research Institute of Bioscience and Biotechnology <br> 125, Gwahak-ro, Yuseong-gu, Daejeon <br> 305-806, Republic of Korea | Signature of a person having the power to represent the International Depositary Authority: <br> Director: Kyung-Sook, Bae <br> Date: May 7, 2012 |

Budapest Treaty on the International Recognition of the Deposit of Microorganisms for the Purposes of Patent Procedure

Attestation Concerning the Later Indication or an Amendment of the Scientific Description and/or Proposed Taxonomic Designation pursuant to Rule 8.2

To: Myung-Jun, Jung

134, Gaegok-ri, Wolgot-myeon, Gimpo-si

Gyeonggi-do 415-872, Republic of Korea

| The enclosed communication has been received by the International Depository Authority on April 27, 2012.<br><br>KCTC 12201BP<br>*Bifidobacterium breve* BR3 → *Bifidobacterium breve* CBT BR3 ||
|---|---|
| International Depository Authority ||
| Name: Biological Resource Center<br>Address: Korea Research Institute of Bioscience and Biotechnology<br>125, Gwahak-ro, Yuseong-gu, Daejeon 305-806, Republic of Korea | Signature of a person having the power to represent the International Depository Authority:<br>Director: Doo-Sang, Park<br>Date: May 6, 2015 |

Enclosure: Communication of the later indication or an amendment of the scientific description and/or taxonomic designation pursuant to Rule 8.1.

Budapest Treaty on the International Recognition of the Deposit of Microorganisms for the Purposes of Patent Procedure

Receipt in the Case of an Original Deposit issued pursuant to Rule 7.1 by the International Depositary Authority

To: Myung-Jun, Jung

134, Gaegok-ri, Wolgot-myeon, Gimpo-si

Gyeonggi-do 415-872, Republic of Korea

| I. Identification of Microorganism | |
|---|---|
| Identification reference given by the Depositor: *Bifidobacterium bifidum* BF3 | Accession number given by the International Depositary Authority: KCTC 12199BP |
| II. Scientific Description and/or Proposed Taxonomic Designation | |
| The microorganism identified under I above was accompanied by: [X] a scientific description [ ] a proposed taxonomic designation (Mark with a cross where applicable) | |
| III. Receipt and Acceptance | |
| This International Depository Authority accepts the microorganism identified under I above, which was received by it on April 27, 2012 | |
| IV. Receipt for Request of Conversion | |
| The microorganism identified under I above was received by this International Depositary Authority on __, and a request to convert the original deposit to a deposit under the Budapest Treaty was received by it on __. | |
| V. International Depository Authority | |
| Name: Biological Resource Center Address: Korea Research Institute of Bioscience and Biotechnology 125, Gwahak-ro, Yuseong-gu, Daejeon 305-806, Republic of Korea | Signature of a person having the power to represent the International Depositary Authority: Director: Kyung-Sook, Bae Date: May 7, 2012 |

Budapest Treaty on the International Recognition of the Deposit of

Microorganisms for the Purposes of Patent Procedure

Attestation Concerning the Later Indication or an Amendment of the Scientific Description and/or Proposed Taxonomic Designation pursuant to Rule 8.2

To: Myung-Jun, Jung

134, Gaegok-ri, Wolgot-myeon, Gimpo-si

Gyeonggi-do 415-872, Republic of Korea

| The enclosed communication has been received by the International Depository Authority on April 27, 2012. <br><br>KCTC 12199BP<br>*Bifidobacterium bifidum* BF3 → *Bifidobacterium bifidum* CBT BF3 ||
|---|---|
| International Depository Authority ||
| Name: Biological Resource Center<br>Address: Korea Research Institute of Bioscience and Biotechnology 125, Gwahak-ro, Yuseong-gu, Daejeon 305-806, Republic of Korea | Signature of a person having the power to represent the International Depository Authority:<br>Director: Doo-Sang, Park<br>Date: May 5, 2015 |

Enclosure: Communication of the later indication or an amendment of the scientific description and/or taxonomic designation pursuant to Rule 8.1.

Budapest Treaty on the International Recognition of the Deposit of Microorganisms for the Purposes of Patent Procedure

Receipt in the Case of an Original Deposit issued pursuant to Rule 7.1 by the International Depositary Authority

To: Myung-Jun, Jung

134, Gaegok-ri, Wolgot-myeon, Gimpo-si

Gyeonggi-do 415-872, Republic of Korea

| I. Identification of Microorganism | |
|---|---|
| Identification reference given by the Depositor:<br>*Bifidobacterium longum* BG7 | Accession number given by the International Depositary Authority:<br>KCTC 12200BP |
| II. Scientific Description and/or Proposed Taxonomic Designation ||
| The microorganism identified under I above was accompanied by:<br>[X] a scientific description<br>[ ] a proposed taxonomic designation<br>(Mark with a cross where applicable) ||
| III. Receipt and Acceptance ||
| This International Depository Authority accepts the microorganism identified under I above, which was received by it on April 27, 2012. ||
| IV. Receipt for Request of Conversion ||
| The microorganism identified under I above was received by this International Depositary Authority on __, and a request to convert the original deposit to a deposit under the Budapest Treaty was received by it on __. ||
| V. International Depository Authority ||
| Name: Biological Resource Center<br>Address: Korea Research Institute of Bioscience and Biotechnology<br>125, Gwahak-ro, Yuseong-gu, Daejeon 305-806, Republic of Korea | Signature of a person having the power to represent the International Depositary Authority:<br>Director: Kyung-Sook, Bae<br>Date: May 7, 2012 |

Budapest Treaty on the International Recognition of the Deposit of

Microorganisms for the Purposes of Patent Procedure

Attestation Concerning the Later Indication or an Amendment of the Scientific Description and/or Proposed Taxonomic Designation pursuant to Rule 8.2

To: Myung-Jun, Jung

134, Gaegok-ri, Wolgot-myeon, Gimpo-si

Gyeonggi-do 415-872, Republic of Korea

| The enclosed communication has been received by the International Depository Authority on April 27, 2012. <br><br>KCTC 12200BP <br>*Bifidobacterium longum* BG7 → *Bifidobacterium longum* CBT BG7 ||
| --- | --- |
| International Depository Authority ||
| Name: Biological Resource Center <br>Address: Korea Research Institute of Bioscience and Biotechnology <br>125, Gwahak-ro, Yuseong-gu, Daejeon 305-806, Republic of Korea | Signature of a person having the power to represent the International Depository Authority: <br>Director: Doo-Sang, Park <br>Date: May 6, 2015 |

Enclosure: Communication of the later indication or an amendment of the scientific description and/or taxonomic designation pursuant to Rule 8.1.

The invention claimed is:

1. A method for alleviating one or more conditions selected from the group consisting of growth retardation, development retardation, and low body weight in a subject selected from the group consisting of human neonates, infants, and growing children, the method comprising administering to the subject a nutraceutical composition, wherein the nutraceutical composition comprises:
an effective amount of *Bifidobacterium longum* CBT BG7 strain deposited under accession number KCTC 12200BP; and
an excipient or a carrier,
wherein said bacteria strain is lyophilized.

2. The method according to claim 1, further comprising orally administering a prebiotic substance.

3. The method according to claim 2, wherein said nutraceutical composition comprises a prebiotic substance and a probiotic substance.

4. The method according to claim 2, wherein said nutraceutical composition further comprises at least one additives selected from the group consisting of a binder, a disintegrant, and a lubricant.

5. The method according to claim 1, wherein said nutraceutical composition further comprises at least one selected from the group consisting of *Bifidobacterium longum* subsp.

*infantis* CBT BT1 (KCTC 11859BP), *Bifidobacterium breve* CBT BR3 (KCTC 12201BP), and *Bifidobacterium bifidum* CBT BF3 (KCTC 12199BP).

6. A method for alleviating one or more conditions selected from the group consisting of growth retardation, development retardation, and low body weight in a subject selected from the group consisting of human neonates, infants, and growing children, the method comprising administering a nutraceutical composition containing an effective amount of *Bifidobacterium longum* species to a subject in need thereof, wherein the nutraceutical composition promotes digestion of a human breast milk.

7. The method according to claim 6, wherein
the *Bifidobacterium longum* species contains β-galactosidase, α-mannosidase, and endo-α-N-acetylgalcotosaminidase genes that encode enzymes that metabolize human milk oligosaccharides.

8. The method according to claim 6, wherein
the *Bifidobacterium longum* species contains a β-glucosidase gene that encodes an enzyme that degrades peptidoglycans of a cell wall of gram-negative pathogenic strains.

9. The method according to claim 6, wherein
the *Bifidobacterium longum* species synthesizes nicotinate (vitamin B3).

10. The method according to claim 6, wherein
the *Bifidobacterium longum* species does not contain a β-glucuronidase gene, and
a resistance of the *Bifidobacterium longum* species to each of antibiotics listed in European Food Safety Authority (EFSA) standards is lower than a break point defined by EFSA.

11. The method according to claim 6, wherein the *Bifidobacterium longum* species is *Bifidobacterium longum* CBT BG7 strain deposited under accession number KCTC 12200BP.

12. The method according to claim 11, wherein the nutraceutical composition contains the *Bifidobacterium longum* species in an amount of $10^8$ to $10^{12}$ cfu/ml.

13. The method according to claim 11, wherein the *Bifidobacterium longum* species is administered with an excipient or a carrier, and said *Bifidobacterium longum* species is lyophilized.

14. The method according to claim 13, wherein the nutraceutical composition further comprises a prebiotic substance.

15. The method according to claim 14, wherein the nutraceutical composition further comprises a probiotic substance.

16. The method according to claim 14, wherein the nutraceutical composition further comprises at least one additive selected from the group consisting of a binder, a disintegrant, and a lubricant.

17. The method according to claim 11, wherein the nutraceutical composition further comprises at least one selected from the group consisting of *Bifidobacterium longum* subsp. *infantis* CBT BT1 (KCTC 11859BP), *Bifidobacterium breve* CBT BR3 (KCTC 12201BP), and *Bifidobacterium bifidum* CBT BF3 (KCTC 12199BP).

* * * * *

SEQUENCE LISTING

<160> NUMBER OF SEQ ID NOS: 1

<210> SEQ ID NO 1
<211> LENGTH: 1518
<212> TYPE: DNA
<213> ORGANISM: Bifidobacterium longum

<400> SEQUENCE: 1

```
agagtttgat cctggctcag gatgaacgct ggcggcgtgc ttaacacatg caagtccaac     60
gggatccatc atgctttgct tggtggtgag agtggcgaac gggtgagtaa tgcgtgaccg    120
acctgcccca tacaccggaa tagctcctgg aaacgggtgg taatgccgga tgctccagtt    180
gatcgcatgg tcttctggga aagctttcgc ggtatgggat ggggtcgcgt cctatcagct    240
tgacggcggg gtaacggccc accgtggctt cgacgggtag ccggcctgag agggcgaccg    300
gccacattgg gactgagata cggcccagac tcctacggga ggcagcagtg gggaatattg    360
cacaatgggc gcaagcctga tgcagcgacg ccgcgtgagg gatggaggcc ttcgggttgt    420
aaacctcttt tatcggggag caagcgtgag tgagtttacc cgttgaataa gcaccggcta    480
actacgtgcc agcagccgcg gtaatacgta gggtgcaagc gttatccgga attattgggc    540
gtaaagggct cgtaggcggt tcgtcgcgtc cggtgtgaaa gtccatcgct taacggtgga    600
tccgcgccgg gtacggcgg gtttgagtgc ggtaggggag actggaattc ccggtgtaac    660
ggtggaatgt gtagatatcg ggaagaacac caatggcgaa ggcaggtctc tgggccgtta    720
ctgacgctga ggagcgaaag cgtggggagc gaacaggatt agataccctg gtagtccacg    780
ccgtaaacgg tggatgctgg atgtggggcc cgttccacgg gttccgtgtc ggagctaacg    840
cgttaagcat cccgcctggg gagtacggcc gcaaggctaa aactcaaaga aattgacggg    900
ggcccgcaca agcggcggag catgcggatt aattcgatgc aacgcgaaga accttacctg    960
ggcttgacat gttcccgacg gtcgtagaga tacggcttcc cttcggggcg ggttcacagg   1020
tggtgcatgg tcgtcgtcag ctcgtgtcgt gagatgttgg gttaagtccc gcaacgagcg   1080
caaccctcgc cccgtgttgc cagcggatta tgccgggaac tcacggggga ccgccggggt   1140
taactcggag gaaggtgggg atgacgtcag atcatcatgc cccttacgtc cagggcttca   1200
cgcatgctac aatggccggt acaacgggat gcgacgcggc gacgcggagc ggatccctga   1260
aaaccggtct cagttcggat cgcagtctgc aactcgactg cgtgaaggcg gagtcgctag   1320
taatcgcgaa tcagcaacgt cgcggtgaat gcgttcccgg gccttgtaca caccgcccgt   1380
caagtcatga aagtgggcag cacccgaagc cggtggccta accccttgtg ggatggagcc   1440
gtctaaggtg aggctcgtga ttgggactaa gtcgtaacaa ggtagccgta ccggaaggtg   1500
cggctggatc acctcctt                                                 1518
```